US012636437B2

(12) United States Patent
Dasbach et al.

(10) Patent No.: US 12,636,437 B2
(45) Date of Patent: May 26, 2026

(54) INJECTOR DEVICE HAVING A BRAKING ARRANGEMENT

(71) Applicant: Sanofi, Paris (FR)

(72) Inventors: Uwe Dasbach, Frankfurt am Main (DE); Kai Scheinert, Frankfurt am Main (DE); Daniel Auernhammer, Frankfurt am Main (DE); Florian Schauderna, Frankfurt am Main (DE); Thomas Mark Kemp, Herts (GB); Tim Schuller, Herts (GB); Robbie Wilson, Herts (GB); Michael Noble, Herts (GB); Ryan Anthony McGinley, Herts (GB)

(73) Assignee: Sanofi, Paris (FR)

( * ) Notice: Subject to any disclaimer, the term of this patent is extended or adjusted under 35 U.S.C. 154(b) by 906 days.

(21) Appl. No.: 17/915,225

(22) PCT Filed: Mar. 31, 2021

(86) PCT No.: PCT/EP2021/058502
§ 371 (c)(1),
(2) Date: Sep. 28, 2022

(87) PCT Pub. No.: WO2021/198370
PCT Pub. Date: Oct. 7, 2021

(65) Prior Publication Data
US 2023/0127858 A1     Apr. 27, 2023

(30) Foreign Application Priority Data
Apr. 3, 2020    (EP) ...................................... 20315117

(51) Int. Cl.
A61M 5/315        (2006.01)
A61M 5/31         (2006.01)

(52) U.S. Cl.
CPC .... A61M 5/31501 (2013.01); A61M 5/31576 (2013.01); A61M 2005/3143 (2013.01);
(Continued)

(58) Field of Classification Search
CPC ........... A61M 2005/3143; A61M 2005/31508; A61M 2005/3151; A61M 5/24;
(Continued)

(56) References Cited

U.S. PATENT DOCUMENTS

2010/0114038 A1     5/2010  Sams
2012/0165753 A1     6/2012  Holmqvist
(Continued)

FOREIGN PATENT DOCUMENTS

CN          102245230 A     11/2011
CN          102448514 A      5/2012
(Continued)

OTHER PUBLICATIONS

International Preliminary Report on Patentability in International Appln. No. PCT/EP2021/058502, mailed on Oct. 13, 2022, 11 pages.
(Continued)

*Primary Examiner* — Shefali D Patel
(74) *Attorney, Agent, or Firm* — Fish & Richardson P.C.

(57)              ABSTRACT
An injector device comprising: an outer housing for receiving a medicament container; and a drive mechanism for dispensing a medicament from the medicament container received in the outer housing. The drive mechanism comprises a plunger rod and a displacing member configured to displace a distal end of the plunger rod into said medicament container to dispense said medicament. The device further comprises a brake configured to slow a rate of displacement of the plunger rod under a force of the displacing member.

15 Claims, 8 Drawing Sheets

(52) U.S. Cl.
CPC ............. *A61M 2005/31508* (2013.01); *A61M 2005/3151* (2013.01)

(58) Field of Classification Search
CPC ................ A61M 5/2422; A61M 5/315; A61M 5/31501; A61M 5/31565; A61M 5/31576
See application file for complete search history.

(56) References Cited

U.S. PATENT DOCUMENTS

| | | | |
|---|---|---|---|
| 2013/0102971 A1 | 4/2013 | Olson | |
| 2016/0317749 A1* | 11/2016 | Jugl ................... | A61M 5/31511 |
| 2017/0348491 A1 | 12/2017 | Kiilerich | |
| 2018/0200446 A1* | 7/2018 | Grimoldby ....... | A61M 5/31501 |
| 2019/0111214 A1* | 4/2019 | Gillespie, III ...... | A61M 5/3245 |

FOREIGN PATENT DOCUMENTS

| | | | |
|---|---|---|---|
| CN | 103118723 | A | 5/2013 |
| CN | 105102025 | A | 11/2015 |
| CN | 105102040 | A | 11/2015 |
| CN | 105283209 | A | 1/2016 |
| CN | 106029131 | A | 10/2016 |
| CN | 110769873 | A | 2/2020 |
| EP | 2585143 | | 12/2018 |
| JP | 2010-508114 | A | 3/2010 |
| JP | 2016-540582 | A | 12/2016 |
| WO | WO 2008/053243 | A2 | 5/2008 |
| WO | WO 2010/066590 | A1 | 6/2010 |
| WO | WO 2010/112563 | A1 | 10/2010 |
| WO | WO 2011/162686 | | 12/2011 |
| WO | WO 2012/022810 | A2 | 2/2012 |
| WO | WO 2014/166889 | A1 | 10/2014 |
| WO | WO 2014/166918 | A1 | 10/2014 |
| WO | WO 2014/191190 | A1 | 12/2014 |
| WO | WO 2015/091763 | A1 | 6/2015 |
| WO | WO 2015/091766 | A1 | 6/2015 |
| WO | WO 2018/215516 | A1 | 11/2018 |
| WO | WO 2018/236619 | A1 | 12/2018 |
| WO | WO 2019/006210 | A1 | 1/2019 |
| WO | WO 2021/198370 | A1 | 10/2021 |

OTHER PUBLICATIONS

International Search Report in International Appln. No. PCT/EP2021/058502, mailed on Apr. 22, 2021, 16 pages.

* cited by examiner

INJECTOR DEVICE HAVING A BRAKING ARRANGEMENT

CROSS REFERENCE TO RELATED APPLICATIONS

The present application is the national stage entry of International Patent Application No. PCT/EP2021/058502, filed on Mar. 31, 2021, and claims priority to Application No. EP 20315117.0, filed on Apr. 3, 2020, the disclosures of which are incorporated herein by reference.

TECHNICAL FIELD

The present disclosure relates to an injector device for a medicament.

BACKGROUND

Injection devices, for example auto-injectors, typically have a sealed container of medicament, and a needle for injection of the medicament into a patient. During injection, a drive mechanism displaces a plunger into the medicament container to dispense medicament through the needle. Normally, a coil spring provides the motive force to displace the plunger. As the coil spring extends, the force exerted by the spring on the plunger decays in accordance with Hook's law. Initially, the spring force is high and dispenses medicament at a high rate. For some patients, this high rate of medicament delivery can be uncomfortable.

SUMMARY

According to the present disclosure, there is provided an injector device comprising:
- an outer housing for receiving a medicament container; and
- a drive mechanism for dispensing medicament from a medicament container received in the outer housing; the drive mechanism comprising a plunger rod and a displacing member configured to displace a distal end of the plunger rod into said medicament container to dispense said medicament;
- wherein the device further comprises a brake configured to control the rate of displacement of the plunger rod under the force of the displacing member.

The displacing member may comprise a spring.

Therefore, the rate of medicament delivery can be slowed for patients who find a relatively higher rate of medicament delivery uncomfortable, particularly at the start of injection where the spring force is high.

The brake may comprise a braking surface that contacts an outer surface of the plunger rod so that movement of the plunger rod is resisted by friction between the braking surface and the outer surface of the plunger rod.

A region of the outer surface of the plunger may be covered with a high friction material, said region being arranged to contact the braking surface of the brake during movement of the plunger between an initial position and an end stop position.

The proportion of the outer surface of the plunger covered by the high friction material may increase toward the distal end of the plunger.

The coefficient of friction of the high friction material may change from a relatively lower coefficient of friction to a relatively higher coefficient of friction toward the distal end of the plunger.

Therefore the friction force between the outer surface of the plunger the braking surface declines as the plunger is displaced, compensating for the decay in the spring force and causing a substantially constant rate of injection.

A region of the outer surface of the plunger may be provided with a channel, said region being arranged to contact the braking surface of the brake during movement of the plunger between an initial position and an end stop position.

The width and/or depth of the channel may decrease towards the distal end of the plunger.

Therefore the contact pressure between the brake and the plunger is reduced as the plunger is displaced to compensate for the decay in the spring force.

The device may further comprise a brake force adjustment mechanism configured to adjust the contact pressure between the braking surface and the outer surface of the plunger rod.

Therefore a user can pre-set an injection speed according to the patient's preference.

The brake force adjustment mechanism may comprise a collar rotatably mounted on the housing, the collar being rotatable around a longitudinal axis of the device to adjust the contact pressure between the braking surface and the outer surface of the plunger rod.

Therefore the injection speed is easily adjusted.

An inner surface of the collar may contact an outer surface of the brake.

Therefore the brake force adjustment mechanism is easily constructed.

The outer surface of the brake may comprise a gradient so that the thickness of the brake increases in a circumferential direction of the device, so that, when the collar is rotated, the contact pressure between the braking surface and the outer surface of the plunger rod varies in dependence on the direction of rotation of the collar.

The inner surface of the collar may comprise a gradient so that the thickness of an inner portion of the collar increases in a circumferential direction of the device, so that, when the collar is rotated, the contact pressure between the braking surface and the outer surface of the plunger rod varies in dependence on the direction of rotation of the collar.

The brake force adjustment mechanism may comprise a sleeve slidably mounted to the housing, the sleeve being configured to slide along a longitudinal axis of the device to adjust the contact pressure between the braking surface and the outer surface of the plunger rod.

Therefore an alternative brake force adjustment mechanism is provided which provides equally easy adjustment of the injection speed.

An inner surface of the sleeve may contact an outer surface of the brake.

The outer surface of the brake may comprise a gradient so that the thickness of the brake increases in a longitudinal direction of the device, so that, the contact pressure between the braking surface and the outer surface of the plunger rod varies in dependence on the direction that the sleeve slides along the longitudinal axis.

The inner surface of the sleeve may comprise a gradient so that the thickness of an inner portion of the sleeve increases in a longitudinal direction of the device, so that, the contact pressure between the braking surface and the outer surface of the plunger rod varies in dependence on the direction that the sleeve slides along the longitudinal axis.

The plunger rod may be tapered so that the diameter of the distal end of the plunger rod is greater than the diameter of a proximal end of the plunger rod.

Therefore the friction force between the outer surface of the plunger the braking surface declines as the plunger is displaced, compensating for the decay in the spring force and causing a substantially constant rate of injection.

Also according to the present disclosure, there is provided a method of operating an injector device comprising displacing a plunger rod of the injector device in a distal direction; and applying a braking force to the plunger rod to slow the rate of displacement of the plunger rod.

The method may further comprise operating a brake force adjustment mechanism of the injector device to adjust a predetermined rate of displacement of the plunger rod.

The method may further comprise operating the brake force adjustment mechanism of the injector device to adjust a predetermined rate of displacement of the plunger rod in response to information about the viscosity of a medicament of the injector device.

BRIEF DESCRIPTION OF THE FIGURES

Embodiments of the present disclosure will now be described, by way of example only, with reference to the accompanying drawings, in which.

DETAILED DESCRIPTION

Figures 1A, 1B:
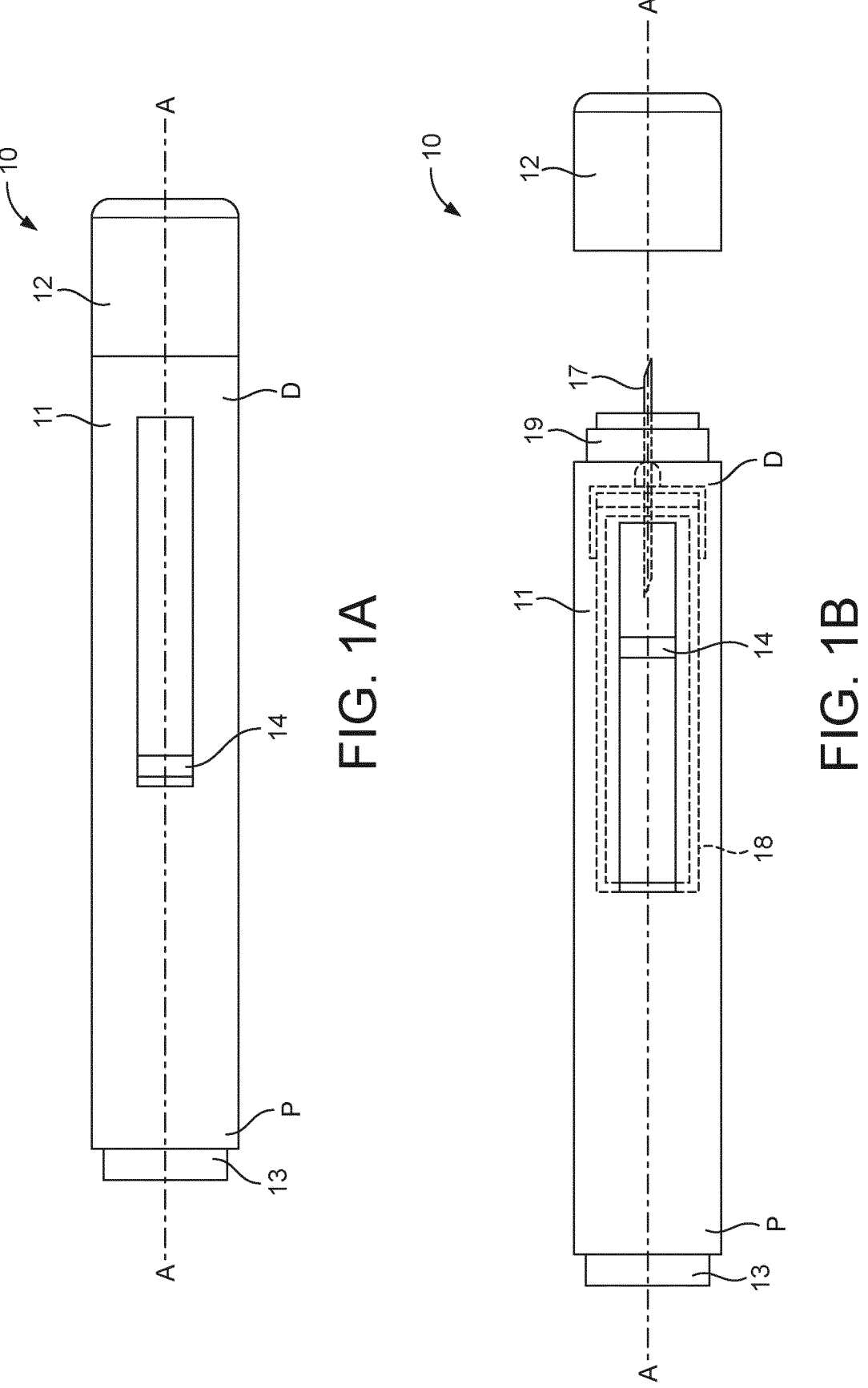
FIG. 1A is a schematic side view of an injector device assembled in accordance with the teachings of the present disclosure, and a removable cap.
FIG. 1B is a schematic side view of the injector device of FIG. 1A, with the cap removed from the housing.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 3 ml. Another device can include a large volume device ("LVD") or patch pump, configured to adhere to a patient's skin for a period of time (e.g., about 5, 15, 30, 60, or 120 minutes) to deliver a "large" volume of medicament (typically about 2 mL to about 50 mL). Yet another device may comprise a pre-filled syringe within a housing of the device. The syringe may be fixed within the housing or may be moveable within the housing, for example from a retracted position to an operation extended position.

In combination with a specific medicament, the presently described devices may also be customized in order to operate within required specifications. For example, the device may be customized to inject a medicament within a certain time period (e.g., about 3 to about 20 seconds for auto-injectors). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A and 1B. Device 10, as described above, is configured to inject a medicament into a patient's body. Device 10 includes a housing 11 which contains a medicament container 18 that defines a reservoir containing the medicament to be injected, and the components required to facilitate one or more steps of the delivery process. The medicament container 18 may be a cartridge or pre-filled syringe.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive mechanism 20 is activated to force medicament from the cartridge 18. The drive mechanism 20 comprises a drive spring 21. The drive spring 21 is under compression before drive mechanism 20 is activated. A proximal end of the drive spring 21 can be fixed within proximal region P of housing 11, and a distal end of the drive spring 21 can be configured to apply a compressive force to a proximal surface of piston 14. Following activation, at least part of the energy stored in the drive spring 21 can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

Figure 2:
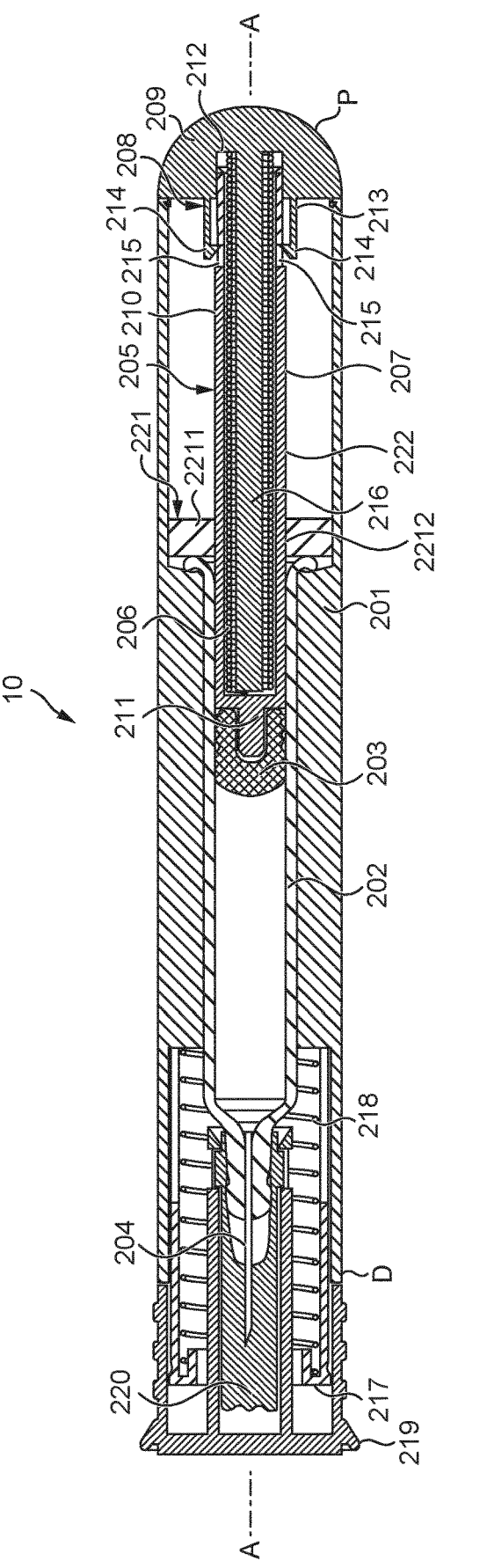
FIG. 2 is a cross section of an example of the device assembled in accordance with the teachings of the present disclosure.

FIG. 2 shows an injector device 10 of one embodiment of the present disclosure.

The injector device 10 comprises an elongate outer housing 201 having a proximal region P and a distal region D. The distal region D is relatively closer to an injection site, and the proximal region P is relatively further away from the injection site. In the present embodiment, the housing 201 has a curved outer surface for more comfortable handling. Preferably, the housing 201 is cylindrical.

A medicament container 202 is supported within the outer housing 201 so that the medicament container 202 is held in fixed relation relative to the housing 201. A proximal end of the medicament container 202 is sealed by a piston 203 which is displaced into the medicament container 202 in use to dispense medicament from the medicament container 202. A needle 204 is provided in fluid communication with a distal end of the medicament container 202. The needle 204 extends beyond a distal end of the housing 201 so that, when the distal end of the housing 201 is pressed up against an injection site, the needle 204 penetrates the injection site for subcutaneous delivery of the medicament.

A drive mechanism 205 is provided within the proximal region P of the housing 201. In use, the drive mechanism 205 is configured to displace the piston 203 into the medicament container 202. The drive mechanism 205 comprises a displacing member 206 (hereinafter a drive spring 206), a plunger 207 and a release mechanism 208. Prior to use, the plunger 207 is held in an initial position against the force of the spring 206 by the release mechanism 208.

A dose delivery button 209 is provided in a proximal end of the housing 201 and is mechanically coupled to the release mechanism 208. During use, the dose delivery button 209 is manipulated by a user to cause the release mechanism 208 to release the plunger 207. The spring 206 then forces the plunger 207 in a distal direction of the device 10. A distal end of the plunger 207 abuts the piston 203 so that the piston 203 is displaced with the plunger 207 to dispense medicament from the medicament container 202.

The plunger 207 comprises an elongate tube 210 with a closed distal end 211. The spring 206 is a coil spring and is disposed within the plunger 207. A distal end of the spring 206 abuts the closed end 211 of the plunger 207, while a proximal end of the spring 206 abuts an inner surface of the device 10. In the illustrated embodiment, the inner surface is an inner surface 212 of the dose delivery button 209.

The release mechanism 208 comprises arms 213 that extend from the inner surface 212 of the dose delivery button 209. Catches 214 are provided at the distal end of each arm 213. The catches 214 are configured to cooperate with a respective aperture 215 in the tubular wall 210 of the plunger 207 to hold the plunger 207 against the force of the spring 206. The catches 214 may be removed from the apertures 215 by manipulation of the dose delivery button 209. For example, the dose delivery button 209 may be rotated to move the arms 213 in a circular fashion about a longitudinal axis A-A of the device 10. In this way, the catches 214 are removed from the apertures 215 and the plunger 207 is then free for displacement under the force of the spring 206.

A spring support 216 extends from the inner surface 212 of the dose delivery button 209 and through the centre of the spring 206. The spring support 216 is configured to support the spring 206 as the plunger 207 is displaced. When the plunger 207 is in the initial position, the spring 206 is disposed almost entirely within the plunger 207. However, during displacement of the plunger 207 the spring 206 extends from the proximal end of the plunger 207 and out of the supporting confines of the plunger's tubular wall 210. The spring support 216 ensures that the spring 206 remains axially aligned with the device as it uncoils.

A needle sleeve 217 is provided in a distal end of the housing 201. The needle sleeve 217 extends from the distal end of the housing 201 to conceal the needle 204 when the needle sleeve 217 is an initial position. The needle sleeve 217 is displaceable into the housing 201 in telescopic fashion to expose the needle 204. The needle sleeve 217 is biased into the initial position by a sleeve spring 218. Therefore, a user may press the distal end of the device 10 up against an injection site to displace the needle sleeve 217 into the housing 201 and to cause the needle 204 to penetrate the injection site.

A cap 219 and needle shield 220 are provided for additional security. The cap 219 locates over the needle sleeve 217 and must be removed with the needle shield 220 prior to use.

During displacement of the plunger 207, the force exerted by the spring 206 on the plunger 207 decays linearly as the spring 206 extends. This will be apparent to any skilled person and can be derived from Hook's law. It shall be appreciated that this effect is not limited to mechanical coil springs and extends to other types of displacing members 206, such as compressed gas actuators and other types of pneumatic or mechanical springs. The illustrated embodiments comprise coil springs 206 by way of example only.

The drop in force due to spring extension causes a corresponding change in the rate at which medicament is dispensed from the medicament container 202: as the spring force decays, so too does the rate at which medicament is dispensed.

Furthermore, the rate of injection can vary depending on the viscosity of the medicament being injected. Medicaments range in viscosity from about 3 cP to about 50 cP and this range will have a corresponding effect on the rate at which medicament is dispensed for a given spring force. Temperature may also affect the viscosity of the medicament and, therefore, the rate at which the medicament is dispensed.

The present disclosure aims to afford the user of the device 10 more control over the rate at which medicament is dispensed and to compensate for the spring force decay and/or variations in the viscosity of the medicament.

It has been determined that pain perception during an injection varies among patients. In some patients, a quick injection is perceived as less painful, whereas in other patients a slow injection is perceived as less painful. Having an inconsistent rate of delivery because of the decaying spring force is likely to cause some discomfort at some stage during injection in a majority of patients.

Therefore, the present disclosure provides a brake 221 to slow the rate of progress of the plunger 207 as it is displaced by the spring 206. The brake 221 comprises a material that is held against the plunger 207 so that the plunger is slowed by friction.

In a first embodiment illustrated in FIG. 2, the brake 221 comprises a cylindrical body 2211 having an inside surface 2212 in contact with an outer surface 222 of the tubular wall 210 of the plunger 207. The body 2211 may be attached to an inner surface of the housing 201 or, as illustrated, the body 2211 may abut a proximal end of the medicament container 202 so that the body 2211 is held in fixed relation relative to the housing 201 during displacement of the plunger 207. Therefore, as the plunger 207 is displaced, the outer surface 222 of the plunger 207 slides across the inside surface 2212 of the body 2211 so that movement of the plunger 207 is resisted by friction between the two surfaces 222, 2212.

Figure 3:
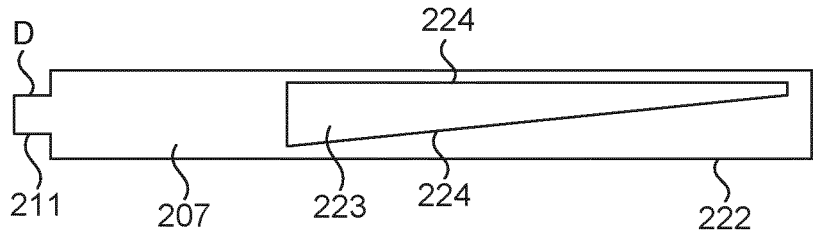
FIG. 3 is a schematic diagram of a plunger in accordance with the teachings of the present disclosure.

In one embodiment, as illustrated in FIG. 3 (in which the plunger 207 is shown in isolation), a region 223 of the outer surface 222 of the plunger 207 is covered with a high friction material. The high friction material causes more friction with the brake 221 than the remaining outer surface of the plunger 207.

The proportion of the outer surface 222 covered by the region of high friction material increases toward the distal end D of the plunger 207. For example, in the illustrated embodiment, opposing edges 224 of the region 223 of high friction material extending longitudinally along the length of the plunger 207 are oblique, so that the width of said region 223 increases toward the distal end D of the plunger 207. Therefore, the friction between the brake 221 and the plunger 207 is reduced as the plunger 207 is displaced. This compensates for the decay in the spring force, so that, as the plunger 207 is displaced by the spring 206, the region 223 of high friction material causes the plunger 207 to move at a constant speed through its full range of movement between the initial position and an end stop position.

Figure 4:
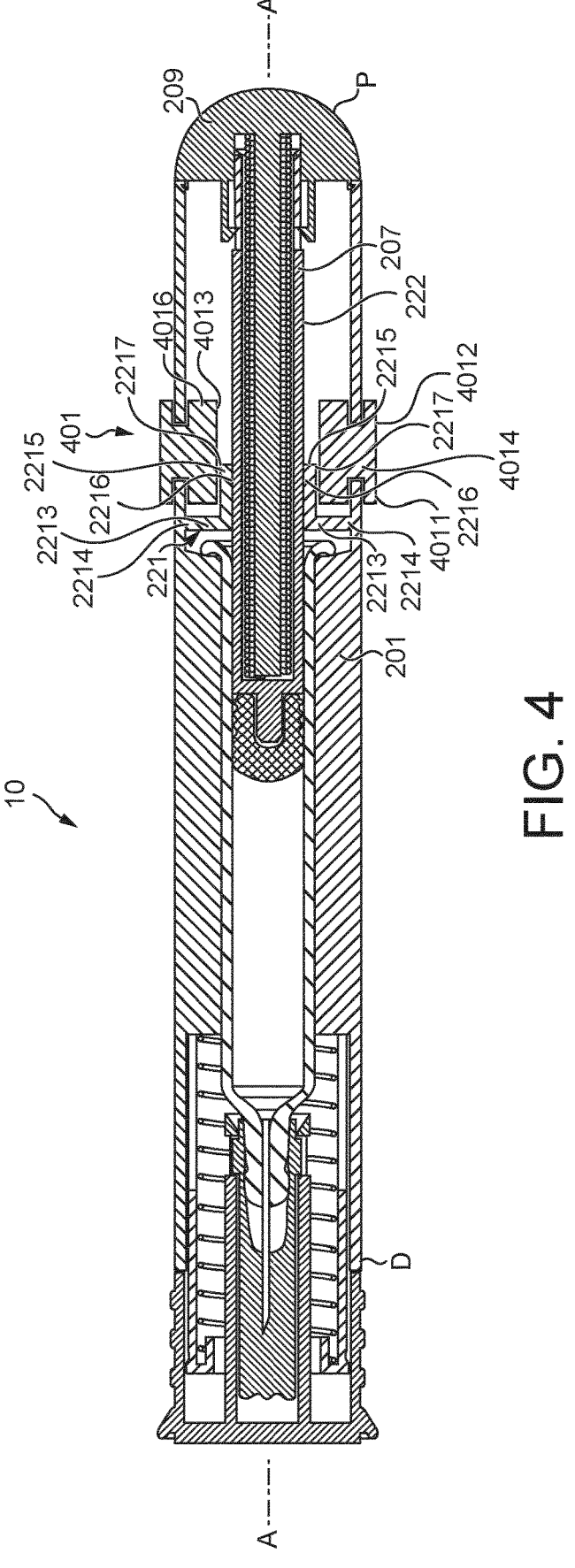
FIG. 4 is a cross section of another example device assembled in accordance with the teachings of the present disclosure.

In another embodiment illustrated by FIG. 4—in which like features retain the same reference numbers—the device further comprises a brake force adjustment mechanism 401. The brake force adjustment mechanism 401 is configured to allow a user to change the speed at which the plunger 207 is displaced, hereinafter referred to as the injection speed. The brake force adjustment mechanism 401 is operable to adjust the force between the brake 221 and the plunger 207, hereinafter referred to as the brake force. Therefore, if a patient would prefer a slower injection, the brake force adjustment mechanism 401 can be used to reduce the injection speed and vice versa. The brake force adjustment mechanism 401 therefore allows the user to control the injection speed in accordance with their preferences. The brake force adjustment mechanism 401 can also be used to compensate for the particular viscosity of the medicament to be injected. For instance, a medicament having a first viscosity would be injected at a first injection speed, while a medicament having a second viscosity, where the second viscosity is higher than the first viscosity, would be injected at a second injection speed, where the second injection speed is slower than the first injection speed. Therefore, if the device is provided with a medicament having a relatively lower viscosity, the user may adjust the brake force adjustment mechanism 401 to increase the brake force and maintain the injection speed as close as possible to their preferred injection speed. Likewise, if the device is provided with a medicament having a relatively higher viscosity, the user may adjust the brake force adjustment mechanism 401 to reduce the brake force and maintain the injection speed as close as possible to their preferred injection speed. In one embodiment the user is provided with information about the viscosity of the medicament and corresponding settings for the brake force adjustment mechanism 401 to allow the user to select from a range of predetermined injection speeds.

In the embodiment illustrated by FIG. 4, the brake force adjustment mechanism 401 comprises a collar 4011 which is supported in the proximal region of the housing 201 overlapping the plunger 207. The collar 4011 is rotatably supported so that a user may rotate the collar 4011 about the longitudinal axis A-A of the device 10. Rotation of the collar 4011 in one direction increases the injection speed, while rotation in the other reduces the injection speed, as will be explained further below.

The collar 4011 comprises an outer surface 4012, which a user can grip to rotate the collar 4011 about the longitudinal axis A-A of the device 10; and an inner surface 4013, which is configured to interact with the brake 221. Rotation of the collar 4011 in one direction presses the brake 221 against the plunger 207 with greater force.

The collar 4011 may be rotated between a first position—representative of a fastest injection speed—and a second position—representative of a slowest injection speed.

In the first position, the brake 221 is pressed against the plunger 207 with the lowest force. In the second position, the brake 221 is pressed against the plunger 207 with the greatest force. Rotation of the collar 4011 between the first and second positions varies the force with which the brake 221 is pressed against the plunger 207. Rotation of the collar 4011 toward the second position increases the force with which the brake 221 is pressed against the plunger 207. Therefore, the collar 4011 can be rotated to fine tune the injection speed to the patient's preference.

In this embodiment, the brake 221 is integrally formed with the housing 201 and comprises at least one arm 2213 which extends from the inner surface of the housing 201. In FIG. 4, two arms 2213 are shown, but it will be appreciated that the brake 221 may comprise a plurality of arms 2213 spaced around the inner surface of the housing 201.

The arms 2213 comprise a hinge 2214 and a brake shoe 2215. The hinge 2214 extends in cantilever fashion away from the inner surface of the housing 201 and toward the plunger 207. The brake shoe 2215 extends from the ends of the hinge 2214 in a longitudinal direction of the device 10. The brake shoe 2215 provides a braking surface 2216 configured to contact the outer surface 222 of the plunger 207.

Opposite the braking surface 2216, an outer surface 2217 of the brake shoe 2215 contacts the inner surface 4013 of the collar 4011. The outer surface 2217 of the brake shoe 2215 is provided with a gradient so that the thickness of the brake shoe 2215 increases in a circumferential direction of the device 10. Therefore, as the collar 4011 is rotated, the contact pressure between the inner surface 4013 of the collar 4011 and the outer surface 2217 of the brake shoe 2215 varies in dependence on the direction of rotation of the collar 4011. If the collar 4011 is rotated in the direction of increasing thickness of the brake shoe 2215, the contact pressure between the inner surface 4013 of the collar 4011 and the outer surface 2217 of the brake shoe 2215 increases. Likewise, if the collar 4011 is rotated in the opposite direction, said contact pressure decreases.

Increasing the contact pressure between the inner surface 4013 of the collar 4011 and the outer surface 2217 of the brake shoe 2215 increases the force with which the brake 221 is pressed against the plunger 207.

The inner and outer surfaces 4013, 4012 of the collar 4011 are connected to each other by at least one connecting portion 4014. The connecting portion 4014 extends through a slot 225 in the housing 201. The slot 225 extends in the circumferential direction to allow rotation of the collar 4011.

Figure 5:
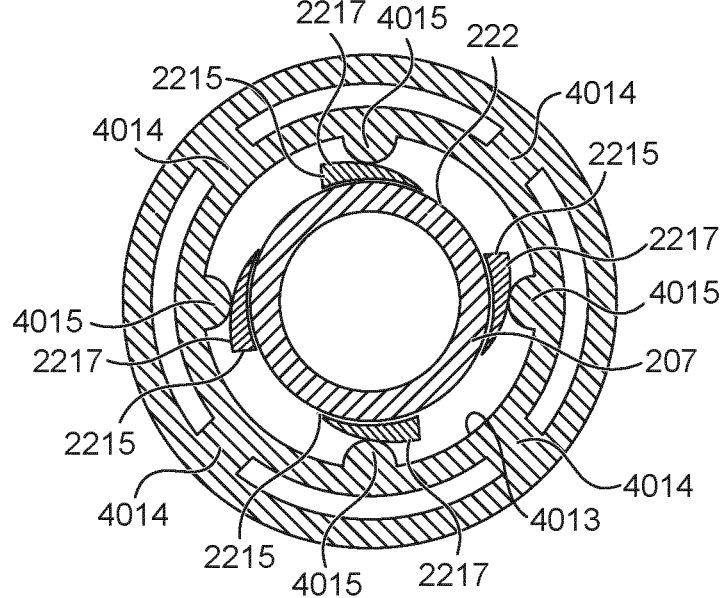
FIG. 5 is a cross section of a brake force adjustment mechanism assembled in accordance with the teachings of the present disclosure.

FIG. 5 shows a cross section of the brake force adjustment mechanism 401 of FIG. 4, taken transversely to the longitudinal axis of the device. In the embodiment illustrated by FIG. 5, the inner surface 4013 of the collar comprises four bumps 4015—in this case hemispherical protuberances of the inner surface 4013—each in contact with an outer surface 2217 of a respective brake shoe 2215. The bumps 4015 and brake shoes 2215 are arranged 90 degrees apart to evenly distribute the pressure applied to the outer surface 222 of the plunger 207. The connecting portions 4014 are also arranged 90 degrees apart and locate in corresponding slots in the housing (not shown).

In an alternative configuration of the embodiment of FIG. 4, the bumps 4015 of the inner surface 4013 of the collar 4011 are omitted and instead the inner surface 4013 is smooth. In this configuration the inner surface 4013 is provided with a gradient so that the thickness of an inner portion 4016 of the collar 4011 increases in a circumferential direction of the device 10. Therefore, as the collar 4011 is rotated, the contact pressure between the inner surface 4013 of the collar 4011 and the outer surface 2217 of the brake shoe 2215 varies in dependence on the direction of rotation of the collar 4011. If the collar 4011 is rotated in the direction of increasing thickness of the inner portion 4016 of the collar 4011, the contact pressure between the inner surface 4013 of the collar 4011 and the outer surface 2217 of the brake shoe 2215 increases. Likewise, if the collar 4011 is rotated in the opposite direction, said contact pressure decreases. In such a configuration, the thickness of the shoe 2215 may be constant in the circumferential direction.

Figure 6:
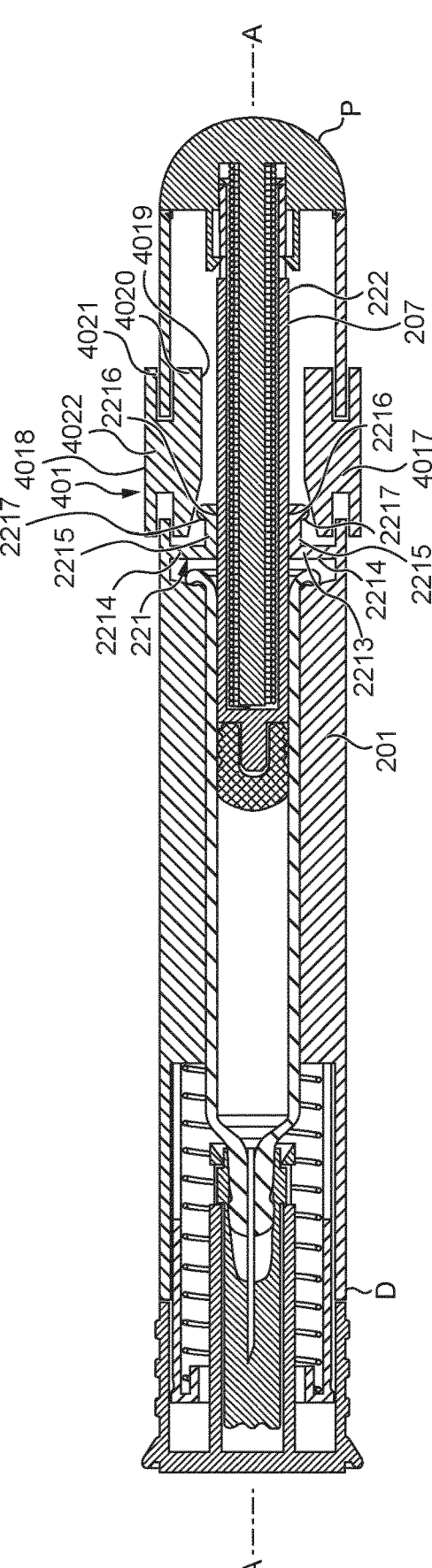
FIG. 6 is a cross section of another example device assembled in accordance with the teachings of the present disclosure.

In another embodiment illustrated by FIG. 6, in which like features retain the same reference numbers, the brake force adjustment mechanism 401 comprises a sleeve 4017 which is supported in the proximal region of the housing 201 overlapping the plunger 207. The sleeve 4017 is slidably supported so that a user may slide the sleeve 4017 along the longitudinal axis A-A of the device 10. Sliding the sleeve 4017 in one direction increases the injection speed, while sliding the sleeve in the other reduces the injection speed, as will be explained below.

The sleeve 4017 comprises an outer surface 4018, which a user can grip to slide the sleeve 4017 along the longitudinal axis of the device 10; and an inner surface 4019, which is configured to interact with the brake 221. Sliding the sleeve 4017 in one direction presses the brake 221 against the plunger 207 with greater force.

The sleeve 4017 may slide between a first position—representative of a fastest injection speed—and a second position—representative of a slowest injection speed.

In the first position, the brake 221 is pressed against the plunger 207 with the lowest force. In the second position, the brake 221 is pressed against the plunger 207 with the greatest force. Sliding the sleeve 4017 between the first and second positions varies the force with which the brake 221 is pressed against the plunger 207. Sliding the sleeve 4017 toward the second position increases the force with which the brake 221 is pressed against the plunger 207. Therefore, the sleeve 4017 slides to fine tune the injection speed to the patient's preference.

In this embodiment—as in the embodiments of FIGS. 4 and 5—the brake 221 is integrally formed with the housing 201 and comprises at least one arm 2213 which extends from the inner surface of the housing 201. In FIG. 6, two arms 2213 are shown, but it will be appreciated that the brake 221 may comprise a plurality of arms 2213 spaced around the inner surface of the housing 201.

The arms 2213 comprise a hinge 2214 and a brake shoe 2215. The hinge 2214 extends away from the inner surface of the housing 201 and toward the plunger 207. The brake shoe 2215 extends from the ends of the hinge 2214 in a longitudinal direction of the device 10. The brake shoe 2215 provides a braking surface 2216 configured to contact the outer surface 222 of the plunger 207.

Opposite the braking surface 2216, an outer surface 2217 of the brake shoe contacts the inner surface 4019 of the sleeve 4017. The inner surface 4019 of the sleeve 4017 is provided with a gradient so that the thickness of an inner portion 4020 of the sleeve 4017 increases in a longitudinal direction of the device. Therefore, the contact pressure between the inner surface 4019 of the sleeve 4017 and the outer surface 2217 of the brake shoe 2215 varies in dependence on the direction in which the sleeve 4017 slides. If a user slides the sleeve 4017 in the direction of increasing thickness of the inner portion 4020 of the sleeve 4017, the contact pressure between the inner surface 4019 of the sleeve 4017 and the outer surface 2217 of the brake shoe 2215 increases. Likewise, if a user slides the sleeve 4017 in the opposite direction, said contact pressure decreases.

Increasing the contact pressure between the inner surface 4019 of the sleeve 4017 and the outer surface 2217 of the brake shoe 2215 increases the force with which the brake 221 is pressed against the plunger 207.

The inner portion 4020 of the sleeve is connected to an outer portion 4021 of the sleeve 4017 by at least one connecting portion 4022. The connecting portion 4022 extends through a slot in the housing 201. The slot extends in the longitudinal direction of the device 10 to allow the sleeve 4017 to slide as described.

Figure 7:
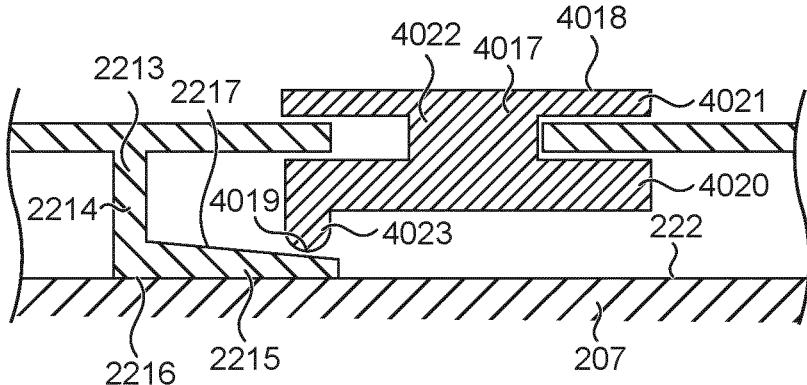
FIG. 7 is a partial, magnified view of another example brake force adjustment mechanism assembled in accordance with the teachings of the present disclosure.

FIG. 7 shows a detail view of an alternative configuration of the embodiment of FIG. 6 in which the outer surface 2217 of the brake shoe 2215 is provided with a gradient so that thickness of the brake shoe 2215 increases in a longitudinal direction of the device 10. In this embodiment, the inner surface 4019 of the sleeve 4017 comprises a bump 4023 that contacts the outer surface 2217 of the brake shoe 2215. Therefore, the contact pressure between the inner surface 4019 of the sleeve 4017 and the outer surface 2217 of the brake shoe 2215 varies in dependence on the direction in which the sleeve 4017 slides. If a user slides the sleeve 4017 in the direction of increasing thickness of the brake shoe 2215, the contact pressure between the inner surface 4019 of the sleeve 4017 and the outer surface 2217 of the brake shoe 2215 increases. Likewise, if a user slides the sleeve 4017 in the opposite direction, said contact pressure decreases.

In the above embodiments the region of high friction material 223 may comprise a plurality of separate regions of high friction material spaced around the outer surface 222 of the plunger 207 so that each separate region of high friction material is in contact with the braking surface 2216 of a respective brake shoe 2215. For example, the plurality of separate regions 223 comprises four separate regions spaced 90 degrees apart.

Figure 8:
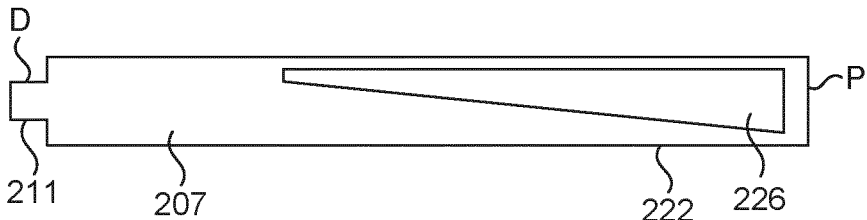
FIG. 8 is another example plunger assembled in accordance with the teachings of the present disclosure.

In the above embodiments, instead of the region of high friction material 223, the plunger 207 may be instead provided with at least one channel 226 in its outer surface 222, as illustrated by FIG. 8. The at least one channel 226 is configured to reduce the contact area between the outer surface 222 of the plunger 207 the braking surface 2216 of a respective brake shoe 2215 overlying the channel 226. The width of the channel 226 increases toward the proximal end P of the plunger 207. Therefore, the proportion of the braking surface 2216 of the brake shoe 2215 overlying the channel 226 increases with displacement of the plunger 207 toward the end stop, reducing the contact area between the outer surface 222 of the plunger 207 and braking surface 2216. Further, the changing width of the channel 226 causes an effective change in the deflection of the brake 221. These effects combined cause a corresponding fall in friction between the braking surface 2216 and the plunger 207 which compensates for the decay in the spring force. The channel is thus configured to cause the plunger 207 to move at a constant speed through its full range of movement between the initial position and the end stop position.

It shall be appreciated that as well as/instead of changing the width of the channel 226, it is also possible to reduce the friction between the braking surface 2216 and the plunger 207 by increasing the depth of the channel 226 toward the proximal end P of the plunger 207. In particular, by increasing the depth of the channel 226 the contact pressure between the braking surface 2216 and the plunger is reduced. In such embodiments, at least part of the braking surface sits within the channel 226.

In the above embodiments, the at least one channel 226 may comprise a plurality of separate channels spaced around the outer surface 222 of the plunger 207 so that each separate channel is disposed below a braking surface 2216 of a respective brake shoe 2215. For example, the plurality of separate channels comprises four separate channels spaced 90 degrees apart.

In the above embodiments, the plunger 207 may be tapered so that an external diameter of the plunger 207 at the distal end of the plunger 207 is marginally greater than the external diameter of the plunger 207 at the proximal end of the plunger 207. Therefore, during displacement of the plunger 207, the contact force between the brake 221 and the plunger 207 is declines as the plunger is displaced toward the end stop position.

The embodiments of injector devices described herein are configured to receive either a cartridge of medicament or a syringe pre-filled with a medicament. Herein, the term "medicament container" is intended to encompass both a cartridge of medicament and a pre-filled syringe.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoylgamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanoates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. An injector device comprising:
a housing for receiving a medicament container;
a drive mechanism for dispensing a medicament from the medicament container received in the housing, the drive mechanism comprising a plunger rod and a displacing member configured to displace a distal end of the plunger rod into the medicament container to dispense the medicament; and a brake configured to control a rate of displacement of the plunger rod under a force of the displacing member,
wherein the brake comprises a braking surface that contacts an outer surface of the plunger rod so that movement of the plunger rod is resisted by friction between the braking surface and the outer surface of the plunger rod,
wherein the injector device comprises a brake force adjustment mechanism configured to adjust a contact pressure between the braking surface and the outer surface of the plunger rod, and
wherein the brake force adjustment mechanism comprises a collar rotatably mounted on the housing, the collar being rotatable around a longitudinal axis of the injector device to adjust the contact pressure between the braking surface and the outer surface of the plunger rod, or
wherein the brake force adjustment mechanism comprises a sleeve slidably mounted to the housing, the sleeve being configured to slide along the longitudinal axis of the injector device to adjust the contact pressure between the braking surface and the outer surface of the plunger rod.

2. The injector device of claim 1, wherein a region of the outer surface of the plunger rod is covered with a high friction material, the region being arranged to contact the braking surface of the brake during movement of the plunger rod between an initial position and an end stop position.

3. The injector device of claim 2, wherein a proportion of the outer surface of the plunger rod covered by the high friction material increases toward the distal end of the plunger rod.

4. The injector device of claim 2, wherein a coefficient of friction of the high friction material changes from a relatively lower coefficient of friction to a relatively higher coefficient of friction toward the distal end of the plunger rod.

5. The injector device of claim 1, wherein a region of the outer surface of the plunger rod is provided with a channel, the region being arranged to contact the braking surface of the brake during movement of the plunger rod between an initial position and an end stop position.

6. The injector device of claim 5, wherein one or more of a width and a depth of the channel decreases towards the distal end of the plunger rod.

7. The injector device of claim 1, wherein an inner surface of the collar contacts an outer surface of the brake.

8. The injector device of claim 7, wherein the outer surface of the brake comprises a gradient so that a thickness of the brake increases in a circumferential direction of the injector device, so that, when the collar is rotated, the contact pressure between the braking surface and the outer surface of the plunger rod varies in dependence on a direction of rotation of the collar.

9. The injector device of claim 7, wherein the inner surface of the collar comprises a gradient so that a thickness of an inner portion of the collar increases in a circumferential direction of the injector device, so that, when the collar is rotated, the contact pressure between the braking surface and the outer surface of the plunger rod varies in dependence on a direction of rotation of the collar.

10. The injector device of claim 1, wherein an inner surface of the sleeve contacts an outer surface of the brake.

11. The injector device of claim 10, wherein the outer surface of the brake comprises a gradient so that a thickness of the brake increases in a longitudinal direction of the injector device, so that, the contact pressure between the braking surface and the outer surface of the plunger rod varies in dependence on a direction that the sleeve slides along the longitudinal axis.

12. The injector device of claim 10, wherein the inner surface of the sleeve comprises a gradient so that a thickness of an inner portion of the sleeve increases in a longitudinal direction of the injector device, so that, the contact pressure between the braking surface and the outer surface of the plunger rod varies in dependence on a direction that the sleeve slides along the longitudinal axis.

13. The injector device of claim 1, wherein the plunger rod is tapered so that a diameter of the distal end of the plunger rod is greater than a diameter of a proximal end of the plunger rod.

14. The injector device of claim 1, comprising the medicament container.

15. A method of operating an injector device that comprises a brake, the method comprising:

displacing a plunger rod of the injector device in a distal
    direction;
applying a braking force to the plunger rod to slow a rate
    of displacement of the plunger rod;
  adjusting a contact pressure between a braking surface of
    the brake and an outer surface of the plunger rod; and
  rotating a collar around a longitudinal axis of the injector
device to adjust the contact pressure between the brak-
    ing surface and the outer surface of the plunger rod; or
  sliding a sleeve along the longitudinal axis of the injector
    device to adjust the contact pressure between the brak-
    ing surface and the outer surface of the plunger rod.

\* \* \* \* \*